(12) United States Patent
Bellesort

(10) Patent No.: US 6,172,130 B1
(45) Date of Patent: Jan. 9, 2001

(54) DENTAL PROSTHESES WITH MODIFIED SURFACE AND METHOD OF PRODUCTION

(76) Inventor: Stèphane Bellesort, 14, rue de la Reine Bérangère, Le Mans (FR), 72000

( * ) Notice: Under 35 U.S.C. 154(b), the term of this patent shall be extended for 0 days.

(21) Appl. No.: 09/171,467

(22) PCT Filed: May 28, 1997

(86) PCT No.: PCT/FR97/00932

§ 371 Date: Oct. 19, 1998

§ 102(e) Date: Oct. 19, 1998

(87) PCT Pub. No.: WO97/45092

PCT Pub. Date: Dec. 4, 1997

(30) Foreign Application Priority Data

May 30, 1996 (FR) .................................................. 96 06680

(51) Int. Cl.[7] .............................. A61F 2/00; A61K 6/083; H05H 1/00
(52) U.S. Cl. .......................... 523/115; 427/226; 427/535; 427/536; 428/543; 523/105; 523/113
(58) Field of Search ..................................... 523/105, 113, 523/116, 115; 427/535, 536, 226; 428/543

(56) References Cited

U.S. PATENT DOCUMENTS

| | | |
|---|---|---|
| 4,504,228 | 3/1985 | Maetani et al. ....................... 433/199 |
| 5,176,951 | * 1/1993 | Rudo . |
| 5,244,654 | * 9/1993 | Narayanan . |

FOREIGN PATENT DOCUMENTS

| | | | |
|---|---|---|---|
| 0 096 573 A2 | 12/1983 | (EP) | ................................ C08J/7/12 |
| 0 373 385 A1 | 6/1990 | (EP) | ............................ C07C/271/16 |
| 0 401 385 | 12/1990 | (EP) | ............................... A61K/6/083 |
| 0 487 418 A1 | 5/1992 | (EP) | ............................... A61L/27/00 |
| 2.111.959 | 6/1972 | (FR) | ............................... B29D/11/00 |

* cited by examiner

*Primary Examiner*—Peter A. Szekely
(74) *Attorney, Agent, or Firm*—Jacobson, Price, Holman & Stern, PLLC

(57) ABSTRACT

Dental prosthesis composed of a polymer containing hydrogen atoms and with the required mechanical and chemical properties, characterized in that the hydrogen atoms on the surface of the said polymer are partially replaced by fluorine atoms in the CF, —$CF_2$—$CF_3$, —OH, —COOH, —C=O, —OOH, —$NH_2$, —C=NH or $CONH_2$ groups. This type of polymer can improve the retention of prostheses and/or limit the development of dental plaque.

9 Claims, No Drawings

DENTAL PROSTHESES WITH MODIFIED SURFACE AND METHOD OF PRODUCTION

This invention relates to dental prostheses with modified surface.

It also relates to a process for manufacturing these prostheses.

There are 10 million persons in France wearing attached dental prostheses. 38% use a complete set of false teeth, 57% use partial false teeth and 5% use both types of false teeth.

Extrapolating across the European Community, the number of persons using false teeth is probably about 60 million.

Partial and complete resin dental prostheses, particularly made of polymethacrylate, have an intermediate surface energy of between 35 and 45 mj.m$^{-2}$. There are two major disadvantages with these prostheses due to this energy and the porosity of the material:

high adhesion of proteins that causes candidiasis, cavities and prosthetic stomatites, and insufficient retention for complete sets of false teeth and mainly complete lower false teeth.

Miscellaneous methods have been used to improve retention of these prostheses. Thus starting in the XVI$^{th}$ century, springs were placed on prostheses between maxillary and mandibular false teeth. Then in the XVIII$^{th}$ century prostheses were treated in a Fauchard vacuum chamber. Finally, repulsive magnets were installed on some prostheses.

More recently, attempts were made to improve prostheses by increasing the surface energy of the component materials. Thus, hydrophile resins were manufactured.

An attempt was also made to cover polymethylmethacrylates with silicon dioxide. However, this process was found to be expensive and the resulting prostheses were unstable.

Patent application EP-0 401 385 (Mitsubishi Rayon Co., limited) describes a treatment for acrylic resin prostheses by a halogen or a halon compound, preferably based on iodine. This treatment has the disadvantages that it modifies the biocompatibility of the resins and increases the volume of the prostheses. Furthermore, this treatment can only avoid the formation of dental plaque, and does not have any effect on the retention of prostheses. Finally iodine, which is the element preferably used, can produce allergies.

The intrados of the prosthesis for complete dental prostheses were also subjected to quartz sanding for 30 to 60 seconds. However, this technique also proved to be unsuitable, due to the considerable increase in bacterial colonization.

Dental adhesives are also used to hold dental prostheses in the mouth. Nevertheless, these adhesives must be used once or several times per day. Furthermore, they are quite expensive.

Resin dental prostheses are also responsible for the development of severe dental plaque. Thus, negative Gram germs are three times more numerous in a person wearing a new prosthesis, and eleven times more numerous in persons wearing old prostheses, compared with a healthy individual with teeth. Enterobacteria are seven times more numerous for a person wearing new prostheses compared with a healthy individual with teeth. Candidiases are eight times more numerous for a person wearing new prostheses and twenty-seven times more numerous for a person wearing old prostheses.

This bacterial plaque creates prosthetic acidosis responsible for cavities, gingivitis, candidiasis and sub-prosthetic stomatitis in persons wearing resin prostheses.

In order to prevent the development of this dental plaque, persons wearing prostheses must maintain strict hygiene and use cleaning products, and must not wear their prostheses at night, which is usually not well perceived by patients.

Therefore, there is no way of providing efficient retention of prostheses, and limiting the development of bacterial plaque to an acceptable level.

The treatment of various objects by cold plasma is well known.

Thus, application FR 2 620 624 (IRAP, CARDIAL, DE LA FAYE) describes various objects designed to come into contact with blood, such as catheters, syringes, parts of vascular prostheses or heart valves, composed of polymers in which the hydrogen atoms present on their exposed surface have been replaced by fluorine atoms or $CF_2$ or $CF_3$ groups. Polymers particularly include polyethylene, poly (vinyl chloride) or poly(ethylene terephthalate). The hydrogen atoms are replaced such that the total fluorine represents not more than 10% of the atoms present on their surface. Objects are treated in plasma containing fluoride for a period varying from a few seconds to about 10 minutes at a power varying from 0.1 watts to 2 watts per liter of capacity of the reaction vessel, and at a pressure of the order of 10 to 10000 Pa.

Application EP-0 487.418 (IRAP, FIDOMI Group) describes devices for ophthalmologic use formed by polymeric substrates, in which the hydrogen atoms present on the surface have been replaced by fluorine atoms or by CF, $CF_2$ or $CF_3$ groups. The total fluorine represents at least 15% of the atoms present on this surface. Polymers may be polymethylmethacrylate (PPMA), a polymer made of 2 hydroxy-ethylmethacrylate (HEMA) of silicon or a polysulfonate. The devices are treated in appropriate fluoride gases for 1 to 20 minutes, at a reaction vessel emission power of between 3 and 10 watts per liter of capacity of the reaction vessel, and at a negative pressure of between 0.1 and 1 torr.

DEJUN LI and JIE ZHAO (1995, J. Adhesion Sci. Technol., Vol.9, pp 1249–1261) describe the treatment of polyurethane objects by cold argon and nitrogen plasma between 1 and 15 minutes, at a power of 100 watts and a pressure of 0.3 to 15 Pa. The authors demonstrate that these treatments induce reductions in the contact angle of water and an increase in the coagulation time. Therefore, these treatments are obviously intended for applications on objects or devices designed to come into contact with the blood.

Application EP-0 096 573 (The United States of America) describes the treatment of textile fibers by cold plasma. No application to prostheses is mentioned.

GEBHARDT et al. (1995, Proceedings, 12$^{th}$ International Symposium on Plasma Chemistry, Minneapolis, Minn., USA, Vol. 1, 155–160) describe the treatment of high density polyethylene sheets (HDPE) by an argon plasma and then grafting of styrene groups and ether 2-(chloroethyl) vinyl groups by exposure to vapors. Therefore, this article does not describe a simple treatment of cold plasma, but a treatment combining a cold plasma treatment step and a chemical treatment step. The authors show that this surface has a better biocompatibility with rat hepathocytes.

An analysis of the state of the art clearly shows that the treatment of dental prostheses by cold plasma has never been described.

Ocular tissues, or blood cells, are quite different from tissues in the mouth. Thus, the buccal cavity contains a much higher number of types of cellular tissues than the ocular cavity. Consequently the characteristics of polymers in contact with these various tissues and of cell types are different, and cannot be transposed from one organ to another.

Therefore, the applicant attempted to determine conditions for treatment of polymers for use in dental prostheses, in order to improve their retention and/or limit the development of dental plaque.

He showed that the treatment of these polymers by cold plasma can solve these problems.

Therefore, this invention relates to dental prostheses composed mainly of a polymer containing hydrogen atoms and with the required mechanical and chemical properties, characterized in that the hydrogen atoms at the surface of the said polymer have been replaced by fluorine atoms, —CF, —$CF_2$, —$CF_3$, —OH, —$CO_2H$, C=O, —OOH, —$NH_2$, —C=NH and/or —$CONH_2$ groups.

According to a first embodiment, the prostheses are complete sets of false teeth to which hydrogen atoms of the said polymer are preferentially replaced by —OH, CO2H, —C=O, —OOH, NH2, —C=NH and/or —CONH2 groups. Preferably, the said polymers are characterized in that their oxygen content has been increased by between 1 and 15%, and even better between 1 and 10%, over a thickness of 30 nm on the surface of the prosthesis.

These polymers are particularly suitable for complete sets of false teeth since they have a higher surface energy than the untreated polymer, and consequently result in improved retention of the prosthesis and lower bacterial colonization. Prostheses with this type of characteristic can be obtained by treatment, in a form appropriate for their use, by an argon, nitrogen, carbon dioxide or oxygen plasma at an emission power of between 1 and 10 watts, and preferably between 2 and 5 watts per liter of capacity of the reaction vessel.

Argon or nitrogen treatments are particularly suitable, since they avoid the formation of fast oxidation groups on the surface of prostheses.

According to a second embodiment of the invention, hydrogen atoms on the surface of the polymer forming the prosthesis are mostly replaced by fluorine atoms, or CF, $CF_2$ or $CF_3$ groups. Preferably 10 to 60%, or even better 20 to 50%, of hydrogen atoms over a thickness of 30 nm at the surface of the said polymer, have been replaced by fluorine atoms, or CF, $CF_2$ or $CF_3$ groups.

Prostheses based on polymers according to this second embodiment of the invention have a lower surface energy and are consequently more suitable for partial false teeth. For partial false teeth, improved retention by surface treatment is not essential since retention is mechanical (hooks, fasteners, buttons, press studs). In any case, these types of polymers limit the formation of dental plaque due to their low surface energy.

Prostheses according to the second embodiment of the invention may be obtained by a process in which they are treated, in a form appropriate for their use, by a plasma with a non-polymerisable molecule containing fluorine in a reaction vessel with an emission power of between 1 and 5 watts per liter of capacity of the reaction vessel.

Regardless of which process is used, the treatment time in the reaction vessel is beneficially between 2 and 20 minutes, and even better between 5 and 15 minutes. The pressure is beneficially between 0.01 and 10 torrs, and even better 0.1 and 1 torr.

Advantageously, the polymer of which the prostheses are formed is a polyethylmethacrylate, a polymethylmethacrylate (PMMA), possibly cross linked, or a mix of these two polymers, or of other acrylic derivatives. It may also be a polymer based on polydimethylsiloxane.

Any other polymer may be used provided that its mechanical and chemical qualities are compatible with the manufacture of dental prostheses, and have hydrogen atoms that can be substituted by other groups of atoms or functions by a treatment using cold plasma.

Therefore, these treatments can solve the problems that arise for the manufacture of dental prostheses. They guarantee the intrinsic chemical and mechanical qualities of these prostheses. This type of process does not modify the geometry of these prostheses. Furthermore, they do not require the use of a solvent or reagent, which prevents chemical contamination of the prostheses.

Finally, they are perfectly stable and reproducible, which guarantees their quality.

Treatments by cold plasma are done using methods known to the expert in the field. They are described in the general handbook: "Plasma Réactifs (Reactive Plasma); A. Ricard, 1995, Editions de la Société Française du Vide (Publication by the French Vacuum Society)".

This invention is illustrated, without being restricted, by the following examples:

EXAMPLE 1

Treatment of Polymethylmethacrylate Prostheses by Plasma without Fluoride

The polymethylmethacrylate dental prosthesis is firstly cleaned in a hexethidine or chlorhexidine solution.

It is then placed on a plate in a capacitive type plasma reaction vessel.

A vacuum is then created by means of a pump, down to a negative pressure of 0.1 torr.

The reaction vessel has a volume of 15 liters, and emits at a wave length of 13.56 MHz.

Each prosthesis is treated for 10 minutes at a power of 50 watts, in oxygen, carbon dioxide, argon or nitrogen. The surface of the prostheses is analyzed over a 30 nm thick layer, showing that the oxygen content increases by the order of 1 to 10% in the case of an argon treatment.

In the case of nitrogen treatment, the oxygen content increases similarly and the nitrogen content is increased by 1 to 5%.

Water contact angles were measured for untreated PPMA, and for PPMA treated by four different plasma. The results are given in the table.

The results obtained are remarkable, since the contact angle is almost halved as shown in the table, which means that the surface energy of the polymer treated in this way is very much increased. The energy respects an equation of type energy=$F(1+\cos\theta)$, where $\theta$ is the contact angle.

Prostheses obtained in this way have improved retention and limited development of dental plaque on the prosthetic intrados.

EXAMPLE 2

Treatment of Prostheses by Plasma with Fluoride

Treatment is done on partial sets of false teeth, using $CF_4$ and $SF_6$ gases containing fluoride, under the conditions described in example 1.

The results obtained show that, unlike the treatments illustrated in example 1, this type of treatment increases the contact angle of water with the polymer and therefore reduces the surface energy.

This reduction in the surface energy reduces the retention of prostheses, but as an example 1, limits adhesion of bacterial plaque on the intrados of the prosthesis.

TABLE

| Control 1 | Control 2 | Control 3 | Control 4 |
|---|---|---|---|
| 77° C. (difference 7° C. on 6 measurements) | 74° C. (difference 10° C. on 6 measurements) | 84° C. (difference 5° C. on 6 measurements) | 78° C. (difference 12° C. on 6 measurements) |

TABLE-continued

| O$_2$ | CO$_2$ | Ar | N$_2$ |
|---|---|---|---|
| 39° C. (difference 14° C. on 6 measurements) | 43° C. (difference 17° C. on 6 measurements) | 42° C. (difference 14° C. on 6 measurements) | 42° C. (difference 12° C. on 6 measurements) |

What is claimed is:

1. A dental prosthesis having a surface, composed of a polymer containing partially-replaced hydrogen atoms on the surface, and wherein the hydrogen atoms on the surface of the said polymer are partially replaced by a member selected from the group consisting of —OH, —COOH, —C=O, —OOH, —NH$_2$, —C=NH and —CONH$_2$ groups.

2. A dental prosthesis according to claim 1, wherein the thus-replaced hydrogen atoms impart an increase of from 1 to 15% in oxygen content over a thickness of 30 nm at the surface of the said polymer.

3. A dental prosthesis according to claim 1, wherein the polymer is a polymethylmethacrylate, polyethylmethacrylate, or a mix of these two polymers or another acrylic polymeric derivative.

4. A dental prosthesis according to claim 1, wherein the said polymer is a polydimethylsiloxane polymer.

5. A process for manufacturing a prosthesis according to claim 1, which comprises treating with an oxygen, argon, carbon dioxide or nitrogen plasma a prosthesis composed of polymer and having a surface with replaceable hydrogen atoms in a reaction vessel with an emission power of between 1 and 10 watts/l of capacity of the reaction vessel.

6. A process according to claim 5 for manufacturing a prosthesis wherein the treating is effected for from 2 to 20 minutes.

7. A prosthesis which is the same as that manufactured by a process according to claim 5.

8. A dental prosthesis according to claim 2, wherein the increase in oxygen content over a thickness of 30 nm at the surface of said polymer is from 1 to 10%.

9. A process according to claim 6 wherein the treating is effected for from 5 to 15 minutes.

* * * * *